Figure 1:
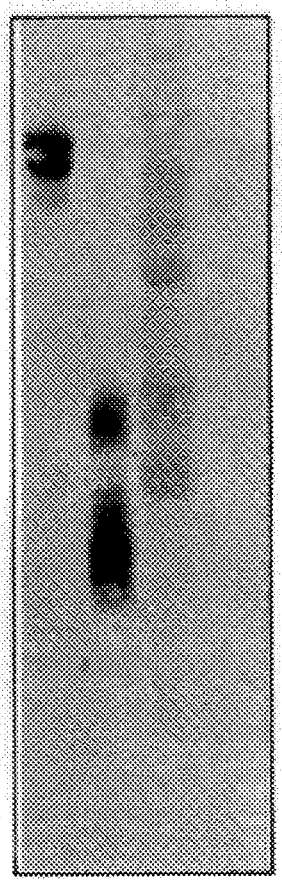

US005663142A

United States Patent [19]

Bouma et al.

[11] Patent Number: 5,663,142

[45] Date of Patent: Sep. 2, 1997

[54] PROTEIN S DELETION VARIANTS DEFICIENT IN C4BP BINDING ACTIVITY, BUT HAVING APC COFACTOR ACTIVITY, COMPOSITIONS AND THERAPEUTIC METHODS

[75] Inventors: Bonno Nammen Bouma, Hilversumsestraatweg 15, NL-3744 KB Baarn; Rogier Maria Bertina, Leiden, both of Netherlands

[73] Assignees: Rijksuniversiteit Leiden, Leiden; Bonno Nammen Bouma, Baarn, both of Netherlands

[21] Appl. No.: 267,387

[22] Filed: Jun. 29, 1994

[30] Foreign Application Priority Data

Jun. 30, 1993 [EP] European Pat. Off. .............. 93201906

[51] Int. Cl.⁶ .......................... A61K 38/17; C07K 14/47
[52] U.S. Cl. ................................. 514/12; 530/380
[58] Field of Search ........................ 530/380; 514/12

[56] References Cited

U.S. PATENT DOCUMENTS 5,321,123  6/1994  Griffin et al. ................ 530/300
5,405,946  4/1995  Griffin et al. ................ 530/380

OTHER PUBLICATIONS

Chang, G.T.G. et al. (1991) "Characterization of thrombin–resistant variants of recombinant human protein S" *Circulation* 86(4):1–814.

Chang, G.T.G. et al. (1992) "The carboxy terminal loop of human protein S is involved in the interaction with human C4b–binding protein" *Blood* 78(10, Suppl. 1):277a.

By R. Nelson et al., "Binding of Protein S to C4b–binding Protein", The Journal of Biological Chemistry, 1992, vol. 267, No. 12, pp. 8140–8145.

*Primary Examiner*—Charles L. Patterson, Jr.
*Assistant Examiner*—Kawai Lau
*Attorney, Agent, or Firm*—Young & Thompson

[57] ABSTRACT

The present invention relates to various functional variants of recombinant protein S (PS) that do not significantly bind C4b binding protein (C4BP) and uses of the variants as a therapeutic reagent. In particular the invention is directed at deletion mutants of protein S, having cofactor activity toward APC and lacking at least the two postulated C4BP binding domains of the SHBG-like domain of the corresponding mature wild type protein S. Such a deletion mutant in particular lacks at least amino acid residues 401–457 and 583–635 of the corresponding mature wild type human protein S.

10 Claims, 5 Drawing Sheets

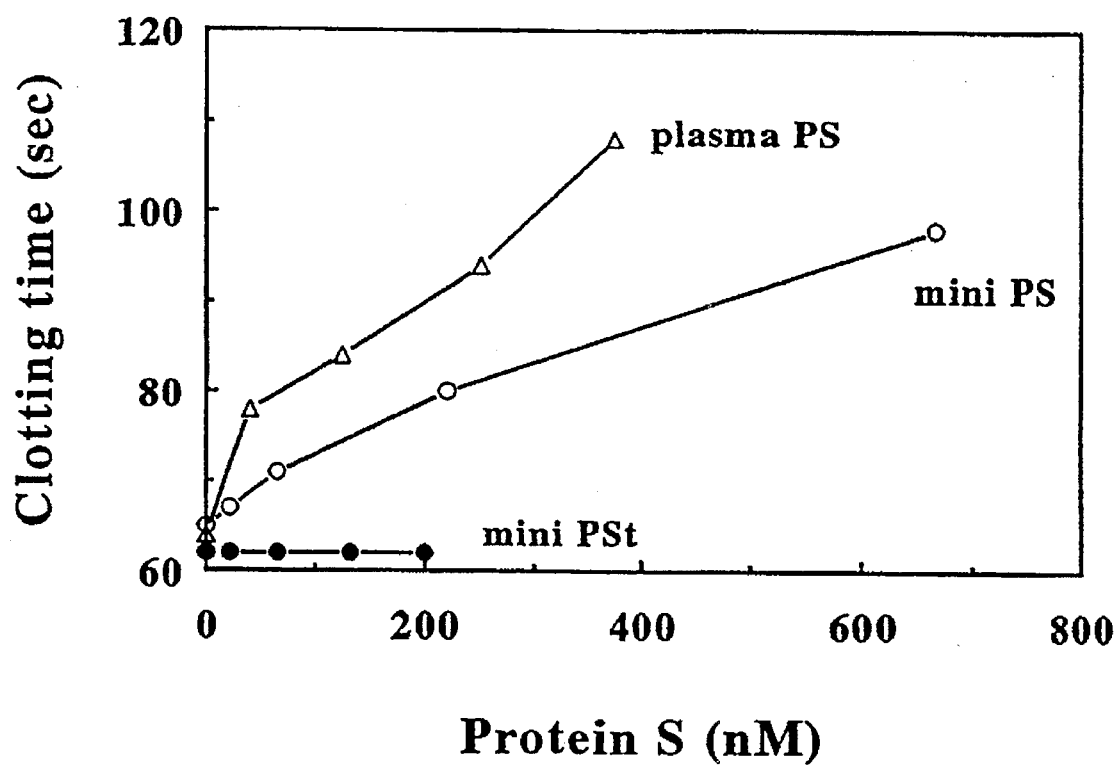

Binding of mini protein S to C4BP
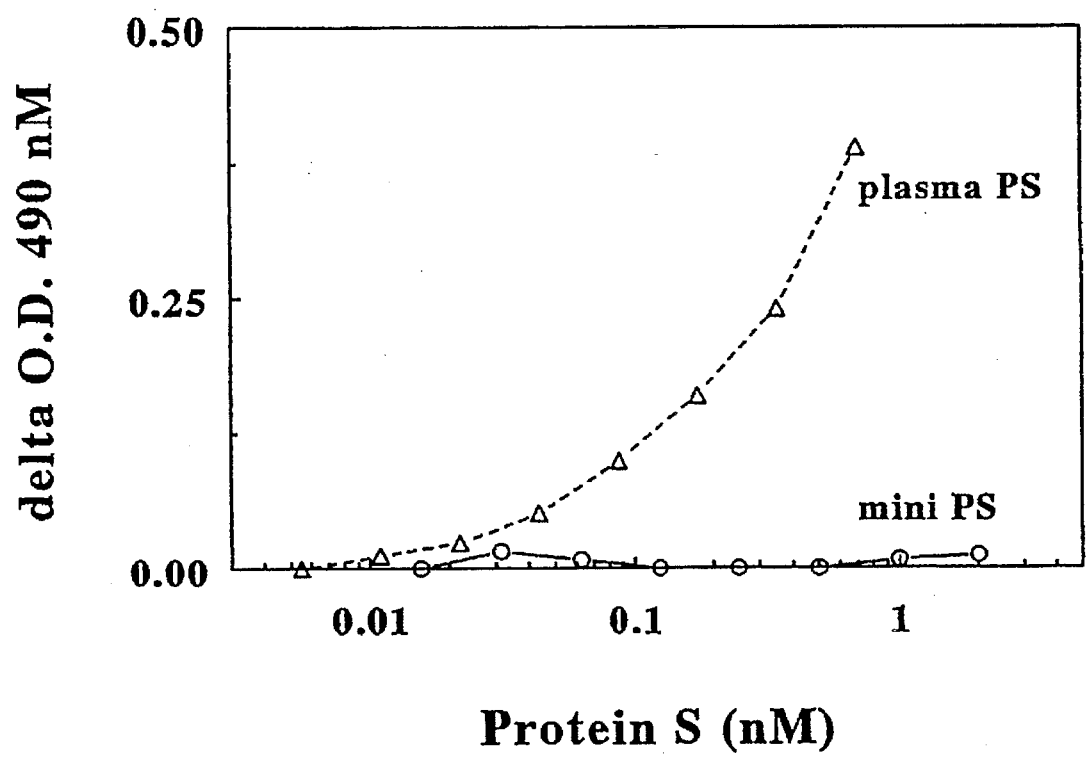

Immuno analysis of mini protein S

PRIMARY STRUCTURE OF HUMAN PROTEIN S

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 3290 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
CTGGCGCGCC  GCGCAGCACG  GCTCAGACCG  AGGCGCACAG  GCTCGCAGCT  CCGGGCGCCT      60

AGCTCCGGTC  CCCGCCGCGA  CGCGCCACCG  TCCCTGCCGG  CGCCTCCGCG  GCTCTCGAAA     120

TGAGGGTCCT  GGGTGGGCGC  TGCGGGGCGC  CGCTGGCGTG  TCTCCTCCTA  GTGCTTCCCG     180

TCTCAGAGGC  AAACCTTCTG  TCAAAGCAAC  AGGCTTCACA  AGTCCTGGTT  AGGAAGCGTC     240

GTGCAAATTC  TTTACTTGAA  GAAACCAAAC  AGGGTAATCT  TGAAAGAGAA  TGCATCGAAG     300

AACTGTGCAA  TAAAGAAGAA  GCCAGGGAGG  TCTTTGAAAA  TGACCCGGAA  ACGGATTATT     360

TTTATCCAAA  ATACTTAGTT  TGTCTTCGCT  CTTTCAAAC   TGGGTTATTC  ACTGCTGCAC     420

GTCAGTCAAC  TAATGCTTAT  CCTGACCTAA  GAAGCTGTGT  CAATGCCATT  CCAGACCAGT     480

GTAGTCCTCT  GCCATGCAAT  GAAGATGGAT  ATATGAGCTG  CAAAGATGGA  AAAGCTTCTT     540

TTACTTGCAC  TTGTAAACCA  GGTTGGCAAG  GAGAAAAGTG  TGAATTTGAC  ATAAATGAAT     600

GCAAAGATCC  CTCAAATATA  AATGGAGGTT  GCAGTCAAAT  TTGTGATAAT  ACACCTGGAA     660
```

-continued

```
GTTACCACTG TTCCTGTAAA AATGGTTTTG TTATGCTTTC AAATAAGAAA GATTGTAAAG      720
ATGTGGATGA ATGCTCTTTG AAGCCAAGCA TTTGTGGCAC AGCTGTGTGC AAGAACATCC      780
CAGGAGATTT TGAATGTGAA TGCCCCGAAG GCTACAGATA TAATCTCAAA TCAAAGTCTT      840
GTGAAGATAT AGATGAATGC TCTGAGAACA TGTGTGCTCA GCTTTGTGTC AATTACCCTG      900
GAGGTTACAC TTGCTATTGT GATGGGAAGA AAGGATTCAA ACTTGCCCAA GATCAGAAGA      960
GTTGTGAGGT TGTTTCAGTG TGCCTTCCCT TGAACCTTGA CACAAAGTAT GAATTACTTT     1020
ACTTGGCGGA GCAGTTTGCA GGGGTTGTTT TATATTTAAA ATTTCGTTTG CCAGAAATCA     1080
GCAGATTTTC AGCAGAATTT GATTTCCGGA CATATGATTC AGAAGGCGTG ATACTGTACG     1140
CAGAATCTAT CGATCACTCA GCGTGGCTCC TGATTGCACT TCGTGGTGGA AAGATTGAAG     1200
TTCAGCTTAA GAATGAACAT ACATCCAAAA TCACAACTGG AGGTGATGTT ATTAATAATG     1260
GTCTATGGAA TATGGTGTCT GTGGAAGAAT TAGAACATAG TATTAGCATT AAAATAGCTA     1320
AAGAAGCTGT GATGGATATA AATAAACCTG GACCCCTTTT TAAGCCGGAA ATGGATTGC      1380
TGGAAACCAA AGTATACTTT GCAGGATTCC CTCGGAAAGT GGAAAGTGAA CTCATTAAAC     1440
CGATTAACCC TCGTCTAGAT GGATGTATAC GAAGCTGGAA TTTGATGAAG CAAGGAGCTT     1500
CTGGAATAAA GGAAATTATT CAAGAAAAAC AAAATAAGCA TTGCCTGGTT ACTGTGGAGA     1560
AGGGCTCCTA CTATCCTGGT TCTGGAATTG CTCAATTTCA CATAGATTAT AATAATGTAT     1620
CCAGTGCTGA GGGTTGGCAT GTAAATGTGA CCTTGAATAT TCGTCCATCC ACGGGCACTG     1680
GTGTTATGCT TGCCTTGGTT TCTGGTAACA ACACAGTGCC CTTTGCTGTG TCCTTGGTGG     1740
ACTCCACCTC TGAAAAATCA CAGGATATTC TGTTATCTGT TGAAAATACT GTAATATATC     1800
GGATACAGGC CCTAAGTCTA TGTTCCGATC AACAATCTCA TCTGGAATTT AGAGTCAACA     1860
GAAACAATCT GGAGTTGTCG ACACCACTTA AATAGAAAC CATCTCCCAT GAAGACCTTC      1920
AAAGACAACT TGCCGTCTTG ACAAAGCAA TGAAAGCAAA AGTGGCCACA TACCTGGGTG      1980
GCCTTCCAGA TGTTCCATTC AGTGCCACAC CAGTGAATGC CTTTTATAAT GGCTGCATGG     2040
AAGTGAATAT TAATGGTGTA CAGTTGGATC TGGATGAAGC CATTTCTAAA CATAATGATA     2100
TTAGAGCTCA CTCATGTCCA TCAGTTTGGA AAAAGACAAA GAATTCTTAA GGCATCTTTT     2160
CTCTGCTTAT AATACCTTTT CCTTGTGTGT AATTATACTT ATGTTTCAAT AACAGCTGAA     2220
GGGTTTTATT TACAATGTGC AGTCTTTGAT TATTTTGTGG TCCTTTCCTG GGATTTTTAA     2280
AAGGTCCTTT GTCAAGGAAA AAAATTCTGT TGTGATATAA ATCACAGTAA AGAAATTCTT     2340
ACTTCTCTTG CTATCTAAGA ATAGTGAAAA ATAACAATTT TAAATTTGAA TTTTTTTCCT     2400
ACAAATGACA GTTTCAATTT TTGTTTGTAA AACTAAATTT TTAATTTTAT CATCATGAAC     2460
TAGTGTCTAA ATACCTATGT TTTTTCAGA AAGCAAGGAA GTAAACTCAA ACAAAAGTGC      2520
GTGTAATTAA ATACTATTAA TCATAGGCAG ATACTATTTT GTTTATGTTT TTGTTTTTTT     2580
CCTGATGAAG GCAGAAGAGA TGGTGGTCTA TTAAATATGA ATTGAATGGA GGGTCCTAAT     2640
GCCTTATTTC AAAACAATTC CTCAGGGGGA CCAGCTTTGG CTTCATCTTT CTCTTGTGTG     2700
GCTTCACATT TAAACCAGTA TCTTTATTGA ATTAGAAAAC AAGTGGGACA TATTTCCTG      2760
AGAGCAGCAC AGGAATCTTC TTCTTGGCAG CTGCAGTCTG TCAGGATGAG ATATCAGATT     2820
AGGTTGGATA GGTGGGGAAA TCTGAAGTGG GTACATTTTT TAAATTTTGC TGTGTGGGTC     2880
ACACAAGGTC TACATTACAA AAGACAGAAT TCAGGGATGG AAAGGAGAAT GAACAAATGT     2940
GGGAGTTCAT AGTTTTCCTT GAATCCAACT TTTAATTACC AGAGTAAGTT GCCAAAATGT     3000
GATTGTTGAA GTACAAAAGG AACTATGAAA ACCAGAACAA ATTTTAACAA AAGGACAACC     3060
```

```
ACAGAGGGAT  ATAGTGAATA  TCGTATCATT  GTAATCAAAG  AAGTAAGGAG  GTAAGATTGC      3120

CACGTGCCTG  CTGGTACTGT  GATGCATTTC  AAGTGGCAGT  TTTATCACGT  TTGAATCTAC      3180

CATTCATAGC  CAGATGTGTA  TCAGATGTTT  CACTGACAGT  TTTAACAAT   AAATTCTTTT      3240

CACTGTATTT  TATATCACTT  ATAATAAATC  GGTGTATAAT  CTAAAAAAA                   3290
```

( 2 ) INFORMATION FOR SEQ ID NO:2:

( i ) SEQUENCE CHARACTERISTICS:
        ( A ) LENGTH: 635 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Ala  Asn  Ser  Leu  Leu  Glu  Glu  Thr  Lys  Gln  Gly  Asn  Leu  Glu  Arg  Glu
  1              5                       10                        15

Cys  Ile  Glu  Glu  Leu  Cys  Asn  Lys  Glu  Glu  Ala  Arg  Glu  Val  Phe  Glu
              20                       25                        30

Asn  Asp  Pro  Glu  Thr  Asp  Tyr  Phe  Tyr  Pro  Lys  Tyr  Leu  Val  Cys  Leu
         35                       40                        45

Arg  Ser  Phe  Gln  Thr  Gly  Leu  Phe  Thr  Ala  Ala  Arg  Gln  Ser  Thr  Asn
    50                       55                        60

Ala  Tyr  Pro  Asp  Leu  Arg  Ser  Cys  Val  Asn  Ala  Ile  Pro  Asp  Gln  Cys
 65                       70                        75                        80

Ser  Pro  Leu  Pro  Cys  Asn  Glu  Asp  Gly  Tyr  Met  Ser  Cys  Lys  Asp  Gly
                   85                       90                        95

Lys  Ala  Ser  Phe  Thr  Cys  Thr  Cys  Lys  Pro  Gly  Trp  Gln  Gly  Glu  Lys
              100                      105                       110

Cys  Glu  Phe  Asp  Ile  Asn  Glu  Cys  Lys  Asp  Pro  Ser  Asn  Ile  Asn  Gly
              115                      120                       125

Gly  Cys  Ser  Gln  Ile  Cys  Asp  Asn  Thr  Pro  Gly  Ser  Tyr  His  Cys  Ser
         130                      135                       140

Cys  Lys  Asn  Gly  Phe  Val  Met  Leu  Ser  Asn  Lys  Lys  Asp  Cys  Lys  Asp
145                       150                      155                       160

Val  Asp  Glu  Cys  Ser  Leu  Lys  Pro  Ser  Ile  Cys  Gly  Thr  Ala  Val  Cys
                   165                      170                       175

Lys  Asn  Ile  Pro  Gly  Asp  Phe  Glu  Cys  Glu  Cys  Pro  Glu  Gly  Tyr  Arg
              180                      185                       190

Tyr  Asn  Leu  Lys  Ser  Lys  Ser  Cys  Glu  Asp  Ile  Asp  Glu  Cys  Ser  Glu
         195                      200                       205

Asn  Met  Cys  Ala  Gln  Leu  Cys  Val  Asn  Tyr  Pro  Gly  Gly  Tyr  Thr  Cys
    210                      215                       220

Tyr  Cys  Asp  Gly  Lys  Lys  Gly  Phe  Lys  Leu  Ala  Gln  Asp  Gln  Lys  Ser
225                       230                      235                       240

Cys  Glu  Val  Val  Ser  Val  Cys  Leu  Pro  Leu  Asn  Leu  Asp  Thr  Lys  Tyr
                   245                      250                       255

Glu  Leu  Leu  Tyr  Leu  Ala  Glu  Gln  Phe  Ala  Gly  Val  Val  Leu  Tyr  Leu
              260                      265                       270

Lys  Phe  Arg  Leu  Pro  Glu  Ile  Ser  Arg  Phe  Ser  Ala  Glu  Phe  Asp  Phe
         275                      280                       285

Arg  Thr  Tyr  Asp  Ser  Glu  Gly  Val  Ile  Leu  Tyr  Ala  Glu  Ser  Ile  Asp
    290                      295                       300

His  Ser  Ala  Trp  Leu  Leu  Ile  Ala  Leu  Arg  Gly  Gly  Lys  Ile  Glu  Val
305                       310                      315                       320
```

```
Gln  Leu  Lys  Asn  Glu  His  Thr  Ser  Lys  Ile  Thr  Thr  Gly  Gly  Asp  Val
               325                      330                          335

Ile  Asn  Asn  Gly  Leu  Trp  Asn  Met  Val  Ser  Val  Glu  Glu  Leu  Glu  His
               340                      345                          350

Ser  Ile  Ser  Ile  Lys  Ile  Ala  Lys  Glu  Ala  Val  Met  Asp  Ile  Asn  Lys
               355                      360                     365

Pro  Gly  Pro  Leu  Phe  Lys  Pro  Glu  Asn  Gly  Leu  Leu  Glu  Thr  Lys  Val
     370                      375                     380

Tyr  Phe  Ala  Gly  Phe  Pro  Arg  Lys  Val  Glu  Ser  Glu  Leu  Ile  Lys  Pro
385                      390                     395                          400

Ile  Asn  Pro  Arg  Leu  Asp  Gly  Cys  Ile  Arg  Ser  Trp  Asn  Leu  Met  Lys
               405                      410                          415

Gln  Gly  Ala  Ser  Gly  Ile  Lys  Glu  Ile  Ile  Gln  Glu  Lys  Gln  Asn  Lys
               420                      425                          430

His  Cys  Leu  Val  Thr  Val  Glu  Lys  Gly  Ser  Tyr  Tyr  Pro  Gly  Ser  Gly
               435                      440                     445

Ile  Ala  Gln  Phe  His  Ile  Asp  Tyr  Asn  Asn  Val  Ser  Ser  Ala  Glu  Gly
     450                      455                     460

Trp  His  Val  Asn  Val  Thr  Leu  Asn  Ile  Arg  Pro  Ser  Thr  Gly  Thr  Gly
465                      470                     475                          480

Val  Met  Leu  Ala  Leu  Val  Ser  Gly  Asn  Asn  Thr  Val  Pro  Phe  Ala  Val
               485                      490                          495

Ser  Leu  Val  Asp  Ser  Thr  Ser  Glu  Lys  Ser  Gln  Asp  Ile  Leu  Leu  Ser
               500                      505                          510

Val  Glu  Asn  Thr  Val  Ile  Tyr  Arg  Ile  Gln  Ala  Leu  Ser  Leu  Cys  Ser
          515                      520                     525

Asp  Gln  Gln  Ser  His  Leu  Glu  Phe  Arg  Val  Asn  Arg  Asn  Asn  Leu  Glu
     530                      535                     540

Leu  Ser  Thr  Pro  Leu  Lys  Ile  Glu  Thr  Ile  Ser  His  Glu  Asp  Leu  Gln
545                      550                     555                          560

Arg  Gln  Leu  Ala  Val  Leu  Asp  Lys  Ala  Met  Lys  Ala  Lys  Val  Ala  Thr
               565                      570                          575

Tyr  Leu  Gly  Gly  Leu  Pro  Asp  Val  Pro  Phe  Ser  Ala  Thr  Pro  Val  Asn
               580                      585                          590

Ala  Phe  Tyr  Asn  Gly  Cys  Met  Glu  Val  Asn  Ile  Asn  Gly  Val  Gln  Leu
               595                      600                     605

Asp  Leu  Asp  Glu  Ala  Ile  Ser  Lys  His  Asn  Asp  Ile  Arg  Ala  His  Ser
     610                      615                     620

Cys  Pro  Ser  Val  Trp  Lys  Lys  Thr  Lys  Asn  Ser
625                      630                     635
```

(2) INFORMATION FOR SEQ ID NO:3:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

CAGAAGAGTT GTGAGTAAGT TTCAGTGTGC CTTCCC        36

PROTEIN S DELETION VARIANTS DEFICIENT IN C4BP BINDING ACTIVITY, BUT HAVING APC COFACTOR ACTIVITY, COMPOSITIONS AND THERAPEUTIC METHODS

TECHNICAL FIELD

The present invention relates to various functional variants of recombinant protein S (PS) that do not significantly bind C4b binding protein (C4BP) and uses of the variants as a therapeutic reagent.

BACKGROUND

Protein S (PS) is a vitamin K-dependent protein of 75,000 molecular weight with 635 amino acid residues. DiScipio et al., *Biochem.*, 18:899 (1979); Lundwall et al., *Proc. Natl. Acad. Sci. USA*, 83:6716–6720 (1986); Hoskins et al., *Proc. Natl. Acad. Sci. USA*, 84:394–353 (1987). Human plasma contains 346 nM PS of which 62% is complexed with the β chain subunit of complement protein, C4b binding protein (C4BP), and 38% is not complexed to C4BP and considered "free PS". Griffin et al., *Blood*, 79:3203–3211 (1992); Dåhlback et al., *Proc. Natl. Acad. Sci. USA*, 78:2512 (1981); Dåhlback et al., *J. Biol Chem.*, 265:16082 (1990); and Nelson et al., *Biochemistry.*, 30:2384 (1991).

PS exhibits anticoagulant activity in in vitro clotting assays. PS demonstrates anticoagulant cofactor activity for activated protein C (APC), an anticoagulant serine protease enzyme. Walker, *J. Biol. Chem.*, 255:5221–5224 (1980); Harris et al., *J. Biol. Chem.*, 260:2007 (1985); Stern et al., *J. Biol. Chem.*, 261:713 (1986); Walker, *J. Biol. Chem.*, 256:11128 (1981); and Solymoss et al., *J. Biol. Chem.*, 263:14884 (1988). PS has also been shown to be an anticoagulant factor in the absence of APC as it can inhibit prothrombinase activity in assays free of APC (Mitchell et al., *Thromb. Haemost.*, 60:298–304, 1988), and binds to Factor Va or Factor Xa and functions as an anticoagulant without APC. Heeb et al., *Circulation*, 86:3238a, 1992; and Heeb et al., *Circulation*, 86:1040a, 1992. In plasma, PS reversibly associates with C4BP with high affinity (dissociation constant of about 1–5 nanomolar). Only free PS is active as an APC cofactor and it is widely accepted that the association of PS with C4BP is associated with loss of the anticoagulant activity of PS. Dåhlback, *J. Biol. Chem.*, 261:12022 (1986); and Taylor et al., *Blood*, 78:357–363 (1991). Therefore, C4BP is effectively an inhibitor of PS anticoagulant activity. The anticoagulant activity of PS can also be diminished or lost by cleavage at arginine residues within the so-called "thrombin-sensitive loop" comprising residues 46–75. Chang et al., *Circulation*, 86:3241a (1992).

PS is physiologically a very important antithrombotic factor since hereditary or acquired deficiencies of PS are associated with venous and arterial thrombotic disease. Allaart et al., *Thromb. Haemost.*, 64:206 (1990); Sie et al., *Thromb. Haemost.*, 62:1040 (1989); Engesser et al., *Ann. Intern. Med.*, 106–677 (1987); Mannucci et al., *Thromb. Haemost.*, 55:44(1986); and Schwartz et al., *Blood*, 74:213 (1989). It is widely accepted that because only free PS has anticoagulant activity in vitro, the level of free PS in blood in vitro is considered the only relevant physiologic anticoagulantly active species. A deficiency of free PS with a normal level of total PS has been described in some patients with thrombotic disease (Comp et al., *Blood*, 67:504, 1986), and it has been hypothesized that an acquired deficiency of free PS due to temporary elevations of C4BP in disseminated intravascular coagulation or in a wide variety of inflammatory conditions, e.g. systemic lupus erythematosus, may contribute to a hypercoagulable state. Taylor et al., *Blood*, 78:357–363 (1991); Heeb et al., *Blood*, 73:455 (1989); Comp et al., *Blood*, 66:348a (1985); D'Angelo et al., *J. Clin. Invest.*, 81:1445 (1988); Boerger et al., *Blood*, 69:692 (1987); and D'Angelo et al., *Ann. Intern. Med.*, 107:42 (1987). In addition, PS has been suggested to be important in metastasizing carcinomas and leukemias and therefore can be used therapeutically to inhibit cancer cell growth. Kemkes-Matthes, Clin. Invest., 70:529–534 (1992).

Recently it was shown in an experimental primate animal model that elevations of C4BP exacerbate host response and convert a nonlethal dose of *E. coli* into a lethal dose. Taylor et al., *Blood*, 78:357–363 (1991). It was also shown that treatment of animals receiving excess PS with the C4BP did not suffer the lethal outcome or the hypercoagulable responses, thus showing that free PS which is not bound to C4BP may be a useful therapeutic agent for infection, inflammation and hypercoagulability. Taylor et al., *Blood*, 78:357–363 (1991). Furthermore, Schwarz et al., have described the use of plasma-derived PS in in vivo therapeutic methods for treating thrombosis and thromboembolic complications. U.S. Pat. No. 5,143,901.

Forms of PS that have reduced affinity for C4BP would provide useful therapeutic agents since they could be administered without risk of loss of activity associated with binding to C4BP.

In Chapter 3 of Glenn T. G. Chang's thesis "Structure and function of human protein S" of Dec. 11, 1992 two deletion variants of protein S are described and have been expressed in C127 cells. The E-variant has a deletion of the third epidermal growth factor like domain (deletion of exon VII corresponding to amino acid residues Asp-160–Asp-202) and expresses normal APC cofactor activity in a plasma system. This activity could be inhibited by the addition of purified C4BP, the binding affinity was similar to that exhibited by wild type.

The second variant (L-variant) which has a deletion of the C-terminal loop of the sex hormone binding globulin (SHBG)-like domain (deletion of exon XV, corresponding to amino acid residues Asp-583 to Ser-635) also expresses normal APC cofactor activity in plasma. This indicates that the third EGF-like domain and the C-terminal part of the SHBG-like domain of protein S are not involved in the expression of the APC cofactor activity of protein S.

The L-variant however shows reduced affinity for binding to C4BP. Due to the failure of monoclonal antibody S12 which recognizes a region close to Ser 460 to bind to the nondenatured L-variant and the recognition of S12 by denatured L-variant, indicating the presence of the S12-epitope on the mutant, it is suggested by Chang that deletion of the C-terminal terminal loop could induce a conformational change that results in a loss of binding affinity for C4BP at a binding site located outside the C-terminal loop of the protein S molecule and that loss of C4BP binding activity does not automatically imply that the C-terminal loop in particular Asp-583 to Serine 635 of the SHBG-like domain of protein S is involved in the interaction with C4BP. The numbering of the residues used by Chang is based on the numbering allocated in Dahlbäck, B., Lundwall, Å., and Stenflo, J. (1986), *Proc. Natl. Acad. Sci. U.S.A.*, 78:2512–2516; Lundwall, Å., Dackowski, W., Cohen, E. Shaffer, M. Marh, A., Dahlbäck, B. Stenflo, J. and Wydro, R. (1986) *Proc. Natl. Acad. Sci. USA*, 83:6716–6720; Hoskins, J., Norman, D. K., Beckman, R. J. and Long, G. L. (1987)

*Proc Natl. Acad. Sci. U.S.A.*, 84:349–35 and Ploos van Amstel, H. K., Van der Zanden, A. L., Reitsma, P. H. and Bertina, R. M. (1987) *FEBS Lett.* 222:186190.

In Fernandez, J. A. and Griffin J. H. (1991) *Thromb. Haemost* 65:711 a C4BP binding site was reported in the center of the SHBG-domain, relatively close to amino acid residue Ser-460 namely amino acid residues 420–434. As monoclonal antibody S12 itself does not interfere with the binding of C4BP to protein S this suggested that the S12 epitope and the Ser-460 region were not involved in the binding to C4BP.

In Chapter 4 of the aforementioned thesis Chang et al. describe mutants comprising substitutions of Glu 424to Lys, Gln-427 to Glu and Lys-429 to Glu in the first disulfide loop. The latter mutant could not bind C4BP and could not recognize an anti-protein S antibody LJ-56 which inhibits complex formation of wild type protein S with C4BP. This confirmed that Lys-429 in the protein is involved in binding to C4BP and it may be concluded that both the first and second disulfide loop of the SHBG-like domain of protein S i.e. residues 408–434 and 598–635 respectively are involved in the interaction with C4BP.

Nelson and Long (Journ. of Biol. Chem. vol. 267, nr. 12, pages 8140–8145, Nelson, R. M. and Long, G. L.) illustrated that deletion of a greater part of the C-terminal loop between amino acid residues Tyr 577 to Ser 635 resulted in a reduced affinity for binding to C4BP, but this deletion leads to a protein without APC cofactor activity. A proper explanation for the lack of anticoagulant activity of Δ577–635 was its lack of full γ-carboxylation. The reason why Δ577–635 was not fully Δ-carboxylated was not evident. Since the cells expressing the rHPS analog were not clonal, it could be a property of the severe truncation itself. While Δ577–635 was not able to function as a cofactor for APC, possibly due to having only about 8 of the usual 10–11 Gla residues and therefore being unable to interact optimally with $Ca^{2+}$, phospholipid, factor Xa and/or APC, it nevertheless binds to the $Ca^{2+}$-dependent monoclonal anti-body used for its purification. This would argue that either the truncation itself directly impedes APC cofactor function, or that APC cofactor function is more stringent in its requirements for Gla than its antibody binding. While the latter seems the more likely explanation for the lack of anticoagulant activity of this mutant it is also a possibility that residues 577–607 confer upon protein S the proper configuration to enable APC cofactor function.

Surprisingly a deletion mutant lacking at least the postulated C4BP binding domain from residues 401–457 and the C4BP binding domain from 583–635 lacks C4BP binding activity but maintained APC cofactor activity. In fact even more surprisingly deletion of the complete C-terminal region known as the SHBG-like domain, i.e. deletion of approximately ⅔ of the wild type protein S without concomitant loss of APC cofactor activity of the resulting deletion mutant has been obtained. Residues 243–635 were removed without destroying the APC cofactor activity of the resulting mini protein S comprising residues 1–242 of the wild type protein S.

The subject invention is directed at a deletion mutant of protein S, having cofactor activity toward APC and lacking at least the two C4BP binding domains of the SHBG-like domain of the corresponding mature wild type protein S. Preferably the activity towards APC of the mutant protein S is no less than 95% of the activity illustrated by the corresponding mature wild type protein S from which the deletion mutant is derived.

In a preferred embodiment of the invention the deletion mutant is derived from human protein S. In the sequence id listing 1 the amino acid sequence of wild type human protein S is given. In this sequence residues 1–37 comprise the Gla domain, residues 38–45 comprise the hydrophobic region, residues 46–75 comprise the thrombin sensitive domain, residues 76–242 comprise the 4 epidermal growth factor like domains and residues 243–635 comprise the SHBG like domain. There are two regions comprising disulfide loops situated within the SHBG like domain at residues 408–434 and 600–625. These two loops are postulated as being the C4BP domains necessary for protein S to bind C4BP as stated earlier in the specification. The invention is therefore in a particular embodiment directed at a deletion mutant human protein S lacking at least amino acid residues 408–434 and 600–625 of the corresponding mature wild type human protein S. A deletion mutant according to the invention can therefore have the amino acid sequence of sequence listing id 1, minus the deleted regions just indicated.

It is also possible for a deletion mutant according to the invention to not just miss the two small regions themselves but also to have a deletion of some or all of the interconnecting amino acid sequence. For human protein S this means a deletion from residue 408 to residue 625. It is also possible to have a deletion from the C-terminus to the end of the second C4BP domain seen from the C-terminal direction. For human protein S this means a deletion from residue 408 to the C-terminal residue. Even more surprisingly it has been discovered that even a deletion of the complete SHBG like domain leads to a deletion mutant that still possesses activity toward APC cofactor. Such a mutant in fact still possesses more than 95% of the activity toward APC that the mature wild type protein S possesses. This is extraordinary as the SHBG-like domain comprises two thirds of the mature wild type protein S and it is generally not expected that such a large deletion will not lead to conformational changes in the rest of the protein leading to inactivation.

The invention is therefore directed at a deletion mutant protein S that has at least a deletion of the C4BP domains and can also comprise further deletions of any size in the amino acid sequence of the SHBG like domain, including deletion of the complete SHBG like domain. For human mutant protein S this means an amino acid sequence according to id 1 comprising a deletion of at least amino acid residues 408–434 and 600–625 and optionally further comprising a deletion of any length in the remaining amino acid sequence located from amino acid residue 243 to the C-terminal amino acid residue leading to a deletion mutant human protein S according to the invention.

The invention describes a modified deletion mutant protein S, a mini protein S designated dPs, which has the desirable properties of:

(1) anticoagulant activity in in vitro coagulation assays; and (2) reduced ability to bind C4b binding protein (C4BP).

By anticoagulant activity is meant that the dPS has the ability to increase the clotting time of protein S deficient plasma in standard in vitro APC cofactor assays, preferably by at least 5%, more preferably by at least 10%, and still more preferably by at least from about 20 to 50%. Representative in vitro coagulation assays are described herein.

The ability of dPs of this invention to bind C4BP is measured in comparison to PS purified from human plasma, or PS produced by recombinant DNA methods, that is, wild-type PS. Preparation of plasma-purified PS has been described by Dahlback et al., *Biochem. J.*, 209:2007–2010 (1983), and by Schwartz et al., U.S. Pat. No. 5,143,901. (The teachings of all references cited are hereby incorporated by reference). Recombinant PS can be produced as described by Chang et al., *Thrombos. Haemost.*, 67:526–532 (1992), or as described herein. A reduced ability of dPS to bind C4BP when compared to wild-type human mature PS binding to C4BP can be any measurable decrease in binding in order to be useful according to this invention, because that reduced binding ability (expressed, for example, as a binding constant) translates into an increased resistance to neutralization by C4BP, an increased plasma level of free protein S, and therefore an effective increase in potency per unit weight of protein.

A preferred reduction in binding ability of C4BP is at least about 50%, preferably at least about 80%, and preferably at least about a 90 to 100% reduction in binding capacity, when measured in direct binding and expressed as a decrease in binding. Stated differently, dPs has less than about 50%, preferably less than 20% to 0% of the C4BP binding capacity of wild-type human mature PS when compared in equivalent C4BP binding assays. Binding of dPS can be measured by a variety of means known to a person skilled in the art.

A dPS of this invention is preferably substantially homologous to the corresponding part of the amino acid sequence encoding wild-type mature PS.

Because dPS is to be used, at least in one embodiment, in methods of treatment in vivo, it is important to present to the patient a protein substantially homologous to the native (wild-type) human PS as to limit possible deleterious immune responses to the protein. By substantially homologous is meant at least 95%, preferably at least 98%, and more preferably at least 99%, of the amino acid residues are the same as in wild-type human mature PS of the corresponding part of the amino acid sequence encoding wild type human mature PS, thereby minimizing the overall differences of the dPS relative to wild-type PS when viewed by the immune system.

The complete amino acid residue sequence of mature wild-type human PS is shown in SEQ ID No. 1. Mature PS refers to the protein after cleavage and removal of the leader polypeptide and signal sequence.

Insofar as protein S from species other than human are highly related both structurally and in terms of primary sequence, the invention also contemplates mutant protein S having the characteristics of dPS which are derived from other mammals, including cow, rat, rabbit, mouse, pig, primates, and the like.

It would obviously be advantageous to produce a mutant protein S not only having cofactor activity for APC and lacking C4BP binding activity but also being resistant to thrombin, as thrombin is known to cleave and inactivate wild type protein S. The invention is therefore also preferably directed at deletion mutants in the various embodiments just described further comprising at least one mutation in the thrombin sensitive loop region of the Gla domain of the corresponding mature wild type protein S, said mutation rendering the deletion mutant thrombin resistant.

It has been described by Chang et al, *Circulation*, 86:3241a (1992), that PS can be mutated at certain arginine residues, namely residues 49, 60 and 70 of wild-type PS, to reduce or eliminate the susceptibility of PS to proteolytic cleavages by thrombin which cause loss of anticoagulant activity. Thrombin-sensitive cleavage sites on PS have been identified to reside at residue positions 49, 60 and 70 in the thrombin sensitive loop region, or T-loop region. Thus, substitutions in this region define a class of mutations referred to as T-loop mutations that form a modified PS. Substitutions of one or more of the residues in the T-loop has been shown to reduce PS susceptibility to thrombin in vitro. Insofar as thrombin cleavage of PS inactivates the anticoagulant activity of PS, inhibition of thrombin sensitivity increases PS activity by increasing its serum half-life. Although the T-loop mutations do not appear to affect the binding of PS to C4BP, mutations in the T-loop do increase resistance to thrombin.

Therefore the subject invention is also directed at a deletion mutant of human protein S as described in the previous paragraph further comprising at least one mutation in the thrombin sensitive loop located in the region defined by residues 46 to 75 of the corresponding mature wild type human protein S. Preferably the mutation in the thrombin sensitive loop is a substitution mutation. Suitable mutation locations in the thrombin sensitive loop are residues at position 49, 60 and 70 of the amino acid sequence of the corresponding wild type mature human protein S.

Thus, the invention contemplates in another embodiment, a deletion mutant PS in which a further mutation comprises substitution of one or more of PS amino acid residue position numbers 49, 60 or 70.

Multiple substitutions are preferred over single substitutions at conferring thrombin resistance. Preferred substitutions are those selected from the group consisting of R49L, R60L and R70I. Particularly preferred substitutions are selected from the group consisting of R49L/R60L, R49L/R70I, R60L/R70I and R49L/R60L/R70I. The triple mutant is most preferred.

Thus a preferred dPS of this invention has a sequence comprising both (1) deletions of the regions responsible for C4BP binding, e.g., amino acid residue positions 401–457 and 583–635 or a deletion of residues 243-C terminal residue, and (2) substitutions in the T-loop region as recited herein. Thus a preferred dPS has one or more substitutions in the thrombin sensitive loop, in addition to at least the deletions of the C4BP binding regions as defined herein.

Another embodiment of the subject invention comprises a further mutation, said further mutation being located in the region comprising epidermal growth factor like domains 3 and 4 in the corresponding wild type mature protein S, preferably in human protein S. Such a mutation can be a substitution or deletion mutant. It is known from Dahlback et al. 1990c (Dahlback, B., Hildebrand, B., Malm J., Characterization of functionally important domains in human vitamin K-dependent protein S using monoclonal antibodies, *J. Biol. Chem.* 1990c; 265:8127–8135) that EGF1 and EGF2 are required for APC cofactor activity. As EGF3 and EGF4 are not required it is possible in addition to the previously mentioned embodiments of the invention to include deletion mutants also lacking the EGF3 and EGF4 domains, i.e. in the region comprised in residues 160–242.

Any deletion mutants according to the invention just described can also undergo any further modifications, i.e. additions, deletions or substitutions that do not decrease the APC cofactor activity. For example it could be possible to make a fusion protein to combine desired characteristics of another protein or polypeptide with the interesting characteristics of the subject deletion mutant.

A deletion mutant protein S (dPS) according to the present invention is used, as discussed further herein, in a variety of therapeutic methods. A dPS can be formulated in pharmaceutical compositions, and can be administered to inhibit coagulation and other PS-mediated processes.

The invention is also directed at a synthetic or recombinant nucleotide sequence encoding an embodiment of a deletion mutant according to the invention and also covers a recombinant vector comprising such a nucleotide sequence, said vector preferably being capable of expressing said nucleotide sequence. The invention also covers a host cell comprising such a nucleotide sequence and/or comprising such a recombinant vector, said host cell preferably being capable of secreting the expression product encoded on said nucleotide sequence or on said vector.

A nucleotide sequence of the present invention is characterized as including a DNA sequence that encodes a deletion mutant protein S (dPS) according to the present invention. That is, a DNA segment of the present invention is characterized by the presence of a dPS structural gene. Preferably the gene is present as an uninterrupted linear series of codons where each codon codes for an amino acid residue found in the dPS protein, i.e. a gene free of introns.

One preferred embodiment is a nucleotide sequence that encodes an amino acid residue sequence that defines a dPS corresponding in sequence to a wild-type PS protein except that the amino acid residue sequence has at least two deletions of the amino acid sequence comprising the two C4BP binding sites, residues 401–457 and 583–635 and preferably a deletion of residues 243-C terminal residue, said nucleotide sequence preferably being capable of expressing a dPS.

A preferred nucleotide sequence codes for an amino acid residue sequence consisting essentially of the sequence shown in SEQ ID NO 2 in which the aforementioned deletions of 401–457 and 583–635 are not present. A DNA sequence corresponding to amino acid sequence id2 is sequence id1. The PS nucleotide sequence id1 is also listed in Gen Bank having accession number Y00692. After post translation processing the corresponding amino acid sequence id2 is obtained. This amino acid residue sequence is also listed in Gen Bank having the accession number A26157.

In a related embodiment, such a nucleotide sequence further contains at least one of the substitutions selected from the group consisting of R49L, R60L and R70I, and the nucleotide sequence is capable of expressing a dPS. A particularly preferred nucleotide sequence includes nucleotide sequences that code for a dPS having substitutions selected from the group consisting of R49L/R60L, R49L/R70I, R60L/R70I and R49L/R60L/R70I. In other words, in one embodiment a nucleotide sequence codes for a dPS having deletions of at least both the C4BP binding domains and substitutions in the T-loop, as described herein.

Homologous DNA and RNA sequences that encode the above dPS are also contemplated.

DNA segments (i.e. synthetic oligonucleotides) that encode dPS proteins can easily be synthesized by chemical techniques, for example, the phosphotriester method of Matteucci, et al., (*J. Am. Chem. Soc.*, 103:3185–3191, 1981) or using automated synthesis methods. In addition, larger DNA segments can readily be prepared by well known methods, such as synthesis of a group of oligonucleotides that define the DNA segment, followed by hybridization and ligation of oligonucleotides to build the complete segment.

Of course, by chemically synthesizing the coding sequence, any desired modifications can be made simply by substituting the appropriate bases for those encoding the native amino acid residue sequence.

In addition, the invention contemplates a recombinant DNA molecule (rDNA) comprising at least a nucleotide sequence of this invention. A rDNA can be produced by operatively linking a vector to a nucleotide sequence of the present invention.

As used herein, the term "vector" refers to a DNA molecule capable of autonomous replication in a cell and to which another nucleotide sequence can be operatively linked so as to bring about replication of the attached segment. A vector capable of directing the expression of a dPS gene is referred to herein as an "expression vector".

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules.

Those vectors that include a procaryotic replicon can also include a procaryotic promoter capable of directing the expression (transcription and translation) of the dPS gene in a bacterial host cell, such as *E. coli*, transformed therewith. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.) and pPL and pKK223 available from Pharmacia, Piscataway, N.J.

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pXT1 available from Stratagene (La Jolla, Calif.), pJ5Eω available from the American Type Culture Collection (ATCC; Rockville, Md.) as accession number ATCC 37722, pTDT1 (ATCC 31255), and the like eucaryotic expression vectors.

The invention also contemplates a host cell transformed with a recombinant DNA molecule of the present invention. The host cell can be either procaryotic of eucaryotic, although eucaryotic cells are preferred. Eucaryotic cells useful for expression of a dPS protein are not limited, so long as the cell line is compatible with cell culture methods and compatible with the propagation of the expression vector and expression of the dPS gene product. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61, NIH Swiss mouse embryo cells NIH/3T3 available from the ATCC as CRL 1658, baby hamster kidney cells (BHK), and the like eucaryotic tissue culture cell lines. Particularly preferred and exemplary is the mouse mammary tumor cell line C127I described by Howley et al., *J. Virol.*, 26:291–298 (1978), and available from the ATCC as ATCC CRL 1616.

Transformation of appropriate cell hosts with a recombinant DNA molecule of the present invention is accomplished by well known methods that typically depend on the type of vector used. With regard to transformation of procaryotic host cells, see, for example, Cohen et al., *Proc. Natl. Acad. Sci. USA*, 69:2110 (1972); and Maniatis et al., *Molecular Cloning, A Laboratory Mammal,* Cold Spring Harbor Laboratory, Cold Spring Harbor, N.Y. (1982).

With regard to transformation of vertebrate cells with vectors containing rDNAs, see, for example, Graham et al.,

*Virol.*, 52:456 (1973); Wigler et al., *Proc. Natl. Acad. Sci. USA*, 76:1373–76 (1979), and the teachings herein.

Successfully transformed cells, i.e., cells that contain a rDNA molecule of the present invention, can be identified by well known techniques, such as that described by Southern, *J. Mol. Biol.*, 98:503 (1975) or Berent et al., *Biotech.*, 3:208 (1985).

In addition to directly assaying for the presence of rDNA, successful transformation can be confirmed by well known immunological methods when the rDNA is capable of directing the expression of dPS, or by the detection of the biological activity of dPS.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains a protein displaying dPS antigenicity or biological activity.

Nutrient media useful for culturing transformed host cells are well known in the art and can be obtained from several commercial sources. In embodiments wherein the host cell is mammalian, a "serum-free" medium can be used. Preferred are the culturing conditions described herein.

Deletion mutant human protein S (dPS) of this invention can be produced by a variety of means, and such production means are not to be considered as limiting.

Preparation of a dPS typically comprises the steps of: providing a DNA segment that codes a dPS protein of this invention; introduction of the provided DNA segment into an expression vector; introduction of the vector into a compatible host cell; culturing the host cell under conditions sufficient for expression of the dPS protein; and harvesting the expressed dPS protein from the host cell.

Insofar as the expressed protein is highly related to wild-type PS, the purification of dPS can be conducted by a variety of art-recognized procedures for preparing purified PS from cell culture.

Thus, in one embodiment, a dPS protein is prepared using a nucleotide sequence as described herein. Alternatively, one can use the screening methods described herein to identify additional substitutions of amino acids in the wild-type PS which produce a dPS having the disclosed desirable properties. As seen by the numerous mutant constructs described herein, a variety of dPS proteins can be produced by the present methods. Additional substitutions (mutations) or deletions other than those described specifically herein can be readily designed to form a dPS having the disclosed biological activities. The mutations can be introduced by any of a variety of procedures, such as in vitro site-directed mutagenesis using preselected oligonucleotides.

Also contemplated are a pharmaceutical composition comprising at least a pharmaceutically acceptable carrier and a deletion mutant protein S according to the invention as active component. Use of a deletion mutant protein S according to the invention as such or as a pharmaceutical composition for treatment of any of the following: a patient at risk for acute thrombosis, protein S deficiency, sepsis, inflammation and cancer also fall within the scope of the invention.

A deletion mutant human protein S (dPS) of the invention is typically provided in one or more of a variety of compositional forms suitable for the contemplated use. Although dPS retains its biological activity in a variety of buffers and solutions, it is preferred to be formulated in a pharmaceutically acceptable excipient. Particularly preferred are compositions which afford maximum stability and biological activity of the dPS in the composition. Such compositions are generally well known in the art.

In one embodiment, a composition can further contain a therapeutically effective amount of a second active ingredient that is effective as an anticoagulant or thrombolytic agent.

Insofar as PS is a calcium dependent protein, preferred compositions further contain divalent calcium cations, typically in a physiological amount.

Therapeutic compositions of the present invention contain a physiologically tolerable carrier together with at least one species of dPS as described herein, dissolved or dispersed therein as an active ingredient. In a preferred embodiment, the therapeutic composition is not immunogenic when administered to a human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like.

In addition, a therapeutic composition is preferably pyrogen free, i.e., incapable of inducing a pyrogenic response when assayed in conventional assays for pyrogens.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified. In addition, a therapeutic amount of dPS can be present in an ointment or on a diffusible patch, such as a bandage, as to afford local delivery of the agent.

In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water, as described herein.

A therapeutic composition contains an effective amount of dPS of the present invention, typically an amount of at least 0.1 weight percent of active protein per weight of total therapeutic composition. A weight percent is a ratio by weight of dPS protein to total composition.

In view of the demonstrated ability of dPS to act as an anticoagulant, coupled with the reduced or absent C4BP binding activity, a dPS of this invention has the ability to function as a useful anticoagulant with increased plasma levels of free PS due to its relative inability to be inactivated by C4BP. Thus, a dPS of this invention can be used therapeutically in place of wild-type protein S (PS) where PS might be used therapeutically. Typical applications for PS, and particularly a dPS of this invention, include coagulative processes in which PS can function to inhibit coagulation, and particularly those processes where C4BP would be present to inhibit PS.

A representative patient for practicing the present methods is any human at risk for thrombosis, inflammation or other deleterious biological processes in which wild-type PS would provide an ameliorative effect.

Exemplary coagulative processes of particular therapeutic importance for a therapeutic method using dPS include acute thrombosis (both venous and/or arterial), hereditary or acquired protein S deficiency, sepsis, inflammation processes, and cancer. The use of PS in arterial and venous thrombosis is particularly preferred, as indicated by several studies; Green, et al., *Neurology*, 42:1029 (1992); Thommen, et al., *Schenlz.med Wschr.*, 119:493–499 (1989); Wiesel, et al., *Thromb. Res.*, 58:461–468 (1990).

The method comprises contacting a tissue, organ, body fluid sample such as blood, plasma or serum, or the circulatory system of a patient, in vivo or in vitro, with a composition comprising a pharmaceutically effective amount of a dPS of this invention. In one embodiment, the contacting in vivo is accomplished by administering a therapeutically effective amount of a physiologically tolerable composition containing a dPS of this invention to a patient.

Thus, the present invention describes in one embodiment a method for inhibiting coagulation in a human comprising administering to the human a composition comprising a therapeutically effective amount of a dPS of this invention.

A therapeutically effective amount of a dPS is a predetermined amount calculated to achieve the desired effect, i.e., to reduce the coagulation time in the body fluid sample of the circulation of the patient, and thereby decrease the likelihood of coagulation. In the case of in vivo therapies, an effective amount can be measured by improvements in one or more symptoms associated with coagulation, inflammation, sepsis or protein S deficiency.

Thus, the dosage ranges for the administration of a dPS of the invention are those large enough to produce the desired effect in which the symptoms of coagulation are ameliorated or the likelihood of coagulation is decreased. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art.

The dosage can be adjusted by the individual physician in the event of any complication.

A therapeutically effective amount of an dPS of this invention is typically an amount such that when administered in a physiologically tolerable composition is sufficient to achieve a plasma or local concentration of from about 1 nanomolar (nM) to 1 micromolar (uM), preferably about 10 to 500 nM, and most preferably about 50 to 200 nM.

The dPS of the invention can be administered parenterally by injection or by gradual infusion over time. The dPS of the invention can be administered intravenously, intraperitoneally, intramuscularly, subcutaneously, intracavitally, transdermally, dermally, and can be delivered by peristaltic means. Because coagulation and inflammation are preferred targets for the present methods, intravenous administration to the circulation is a particularly preferred route.

Representative therapeutic methods, describing exemplary dosages and routes of administration, using PS that are applicable to the present methods using dPS, are described in U.S. Pat. No. 5,143,901 to Schwarz et al.

In a related embodiment, the invention contemplates the use of dPS in combination with other anticoagulation therapies. In particular, in view of PS as a cofactor to activated protein C (APC), a preferred embodiment utilizes dPS therapeutic compositions in combination with therapeutically effective amounts of protein C (PC) zymogen or APC. PC is known to be converted in vivo to APC, and can therefore be used in place of or in combination with APC in in vivo methods. Therefore, in one embodiment the invention contemplates a method of inhibiting coagulation comprising the administration of both a therapeutically effective amount of dPS and a therapeutically effective amount of PC, APC or both, each in a pharmaceutically acceptable excipient. A representative procedure using native PS and APC is described in U.S. Pat. No. 5,143,901 to Schwarz et al., as is the preparation of purified APC suitable for therapeutic use.

EXAMPLE construction of human mini protein S and analysis thereof.

A recombinant human protein S molecule that lacks the human sex hormone binding globulin (SHBG) like domain (mini protein S, residues 1–242) was constructed. The truncated molecule was expressed in a mammalian cell expression system, purified from the cell culture medium and characterized.

On reduced SDS polyacrylamide gel electrophoresis the molecular weight of mini protein S was assessed.

Using an activated partial thromboplastin time clotting assay system mini protein S was able to dose dependently enhance the activated protein C induced clotting time of protein S deficient plasma.

Furthermore, mini protein S was probed with a panel of anti-protein S monoclonal antibodies.

Finally, mini protein S did not interact with C4b-binding protein (C4BP) in a system using purified proteins, suggesting the binding site for C4BP to be localized in the SHBG-like domain.

Experimental Procedures

Materials—Restriction endonucleases BamH I, Xba I Bgl II and Hind III were purchased from Pharmacia Biotechnology (Uppsala, Sweden). T4 DNA Ligase was from Bethesda Research Laboratory (Bethesda, Mass., U.S.A.). All enzymes were used according to the manufacturers instructions. *Escherichia coli* strains CJ236 and XL-1 blue were from Bio-Rad (Richmond, Calif., U.S.A.). APC, protein S and C4BP depleted plasma was prepared as described (Koedam, J. A., Meijers, J. C. M., Sixma, J. J. and Bouma, B. N. (1988) *J. Clin. Invest.* 82, 1236–1243). C4BP and anti-C4BP monoclonal antibodies 8C11, directed against the α-chain of C4BP was prepared as described (Hessing, M., Vlooswijk, R. A. A., Hackeng, T., Kanters, D. and Bouma, B. N. (1990) *J. Immunol.* 144, 204–208). Rabbit anti human protein S IgG conjugated to peroxidase were from Dakopatts (Glostrup, Denmark). Monoclonal antibodies were prepared as described (Hackeng, T. M., Hessing, M., van 't Veer, C., Meijer-Huizinga, E., Meijers, J. C. M., De Groot, P. G., Van Mourik, J. A. and Bouma, B. N. (1993) *J. Biol. Chem.* vol 268, p3993–4000). Iscoves Dulbeccos Modified Medium, pennicillin, streptomycin sulphate, glutamine and fetal calf serum were from Gibco (Paisly Park, UK). Trasylol was from Bayer (Leverkusen, FRG). Vitamin $K_1$ (Konakion) was from F. Hoffman-La Roche (Basel, Switzerland). Vectastain ABC kit was obtained from Vector Laboratories, Burlingame, Calif., U.S.A.

Site Directed Mutagenesis—A 2808-base pair Hind III-BamH I fragment from the expression vector pMSVS (Chang, G. T. G., Ploos van Amstel, H. K., Hessing, M., Reitsma, P. H., Bertina, R. M. and Bouma, B. N. (1992) *Thromb. Haemost.* 67, 526–53221) carrying the Protein S cDNA sequence was subcloned into M13mp19 after digestion with Hind III and Bgl II. The following 36-mer was used as primer: 5'-CAG AAG AGT TaT GAG TAA GTT TCA GTG TGC CTT CCC-3 to hybridize with the nucleotide sequence encoding the amino acid sequence between residues 238–249. The codon TAA at position 243 is a stop codon, therefore the recombinant protein is 242 amino acids long. Underlined nucleotides were altered. Site directed mutagenesis was performed according to Kunkel (Kunkel, T. A. (1985) Proc. Natl. Acad. Sci. USA 82, 488–492). The M13mp19 clone carrying the protein S insert was infected into CJ236 (dut⁻ung⁻) cells and uracil-containing single stranded phage DNA was isolated and used as template. After second strand synthesis with T7 DNA Polymerase and ligation with T4 DNA Ligase competent XL-I blue (dut⁺ ung⁺) cells were transformed. Single stranded DNA from individual resultant plaques was isolated and sequenced by the dideoxy chain termination method (Sanger, F., Nicklen, S. and Coulson, A. R. (1977) Proc. Natl. Acad. Sci. USA 76, 5463–5467) to confirm the sequence was as expected. Double-stranded phage DNA was isolated from bacterial cells and the protein S insert isolated, after Hind III and Xba I digestion and recloned into pMSVPS. The BPV-1 genome was isolated after BamH I digestion of pTZX-BPV as described before (Chang, G. T. G., Ploos van Amstel, H. K., Hessing, M., Reitsma, P. H., Bertina, R. M. and Bouma, B. N. (1992) Thromb. Haemost. 67, 526–532) and cloned into pMSVPS. The resulting plasmid was purified by polyethylene glycol precipitation and deposited at the CBS in Baarn, the Netherlands on Jun. 24, 1993 under accession number 36193 in accordance with the Budapest Treaty.

Cell Culture, DNA transfection and Purification of Recombinant Mini Protein S-C127 cells (ATCC CRL 1616) were cultured as described before (Chang, G. T. G., Ploos van Amstel, H. K., Hessing, M., Reitsma, P. H., Bertina, R. M. and Bouma, B. N. (1992) Thromb. Haemost. 67, 526–532). For transfections 20 µg of plasmids were used and cells were transfected by conventional calcium phosphate coprecipitation technique (Graham, F. and van der Eb, A. (1983) Virology 52, 456–467). The conditioned medium containing recombinant protein S, as determined by an ELISA, was harvested after 48 h of expression in the presence of vitamin $K_1$ (Konakion, Roche, 5 µg/ml). Recombinant protein S was purified on an anion exchange column (Fast Flow Q resin, Pharmacia) as described (Chang, G. T. G., Ploos van Amstel, H. K., Hassing, M., Reitsma, P. H., Bertina, R. M. and Bouma, B. N. (1992) Thromb. Haemost. 67, 526–532). The purity and integrity of the recombinant protein S were judged after separation with SDS/PAGE on reduced 12.5% gels (Laemmli, U. K. (1970) Nature 227, 608–695) and immunoblotting (Towbin, H. J., Staehlin, T. and Gordon J. (1979) Proc. Natl. Acad. Sci. USA 76, 4350–435426) using rabbit anti-protein S polyclonal and mouse anti-protein S monoclonal antibodies.

Protein S Assays—Protein S antigen was determined using a specific monoclonal antibody ELISA. IgG of two independent anti-protein S monoclonal antibodies (13 and 3D9, 5 µg/ml each) were coated in 50 mM $NaHCO_3$, pH 9.6 overnight at 4° C. on to polyvinyl microtiter plates (Costar, Cambridge, Mass., U.S.A.).

After washing of unbound IgGs, the wells were blocked with 1% (w/v) BSA in 50 mM Tris-HCI pH 7.5 containing 150 mM NaCl and 5 mM $CaCl_2$ for 1 h at room temperature. Increasing amounts of recombinant protein S were added and incubated for 18 h at room temperature. Bound protein S was allowed to bind to anti-protein S monoclonal antibody 18 IgG conjugated to biotin (0.5 µg/ml) for 1 h. ABC reagent was added (100 µl) and incubated for 1 h at room temperature. The hydrolysis of nitrophenylphosphate was measured at 492 nm using a $V_{max}$ plate reader (Molecular Devices Corporation, Menlo Park, Calif., U.S.A.).

APC cofactor activity was determined in a clotting assay as described by Chang, G. T. G., Ploos van Amstel, H. K., Hessing, M., Retisma, P. H., Bertina, R. M. and Bouma, B. N. (1992) Thromb. Haemost. 67, 526–532).

Binding of Recombinant Protein S to C4BP—The complex formation between the recombinant protein S and C4BP was measured with a sensitive ELISA using C4BP and a biotin conjugated anti-protein S monoclonal antibody 18. Briefly, IgG (10 µg/ml) from monoclonal antibody 8C11, which is directed against the α-chain of C4BP was coated in 50 mM $NaHCO_3$, pH 9.6 overnight at 4° C. on to polyvinyl microtiter plates (Costar, Cambridge, Mass., U.S.A.). After washing of unbound IgGs, the wells were blocked with 1% (w/v) BSA in 50 mM Tris-HCI pH 7.5 containing 150 mM NaCl and 5 mM $CaCl_2$ for 1 h at room temperature and C4BP was allowed to bind for 2 h with a final concentration of 1 µg/ml. Increasing amounts of recombinant protein S were added and incubated for 18 h at room temperature. Bound protein S was allowed to bind to anti-protein S IgG monoclonal antibody 18 conjugated to biotin (0.5 µg/ml) as described earlier.

Inactivation of Protein S by Thrombin—One ml of recombinant protein S (50 µg/ml) was incubated with 50 µl of thrombin-Sepharose (1 mg/ml) for 1 h at 37° C. in 50 mM Tris-HCI pH 7.5 containing 150 mM NaCl. Thrombin-Sepharose was removed by centrifugation and inactivated protein S was stored at −20° C. until needed.

Binding of Mini Protein S to Anti-Protein S Monoclonal Antibodies—Recombinant or mini protein S (900 ng) were coated on to polyvinyl microtiter plates in 50 mM $NaHCO_3$, pH 9.6 overnight at 4° C. IgG of different monoclonal antibodies (0–1.5 µg/ml) were added and incubated for 2 h at room temperature. The hydrolysis of nitrophenyl phosphate was measured at 492 nm using a $V_{max}$ plate reader (Molecular Devices Corporation, Menlo Park, Calif., U.S.A.).

Results end Discussion

To study the role of the SHBG-like domain of protein S, mini protein S (residues 1–242) was constructed and was expressed in C127 cells. Foci producing recombinant mini protein S as determined by an ELISA were isolated and subcloned using 1 cell/well. The highest protein S producing clone was used for large-scale production of mini protein S. Mini protein S was purified from the culture medium using a Fast Flow Q column. On reduced SDS gels mini protein S had lower apparent molecular masses of 30 and 20 kD (FIG. 1). The upper band represented mature protein S (residues 1–242) and could be converted into the lower band by thrombin (residues 71–242).

The cofactor activity for APC was measured in an activated partial thromboplastin time system using protein S and C4BP depleted plasma and increasing amounts of protein S. FIG. 2 demonstrates that mini protein S possesses cofactor activity to APC, which could be inhibited by thrombin. The cofactor activity was two-fold lower compared to wild type protein S on a molar basis. This could be due to the amount of cleaved material in the mini protein S preparation. At this stage mini protein S contained 80% cleaved material, whereas wild type protein S contained 50% (FIG. 1). This experiment further demonstrates that deletion of the SHBG-like domain does not affect the APC cofactor activity and shows that the interaction of protein S with APC probably occurs via the N-terminus as recently reported by Dahlback and coworkers using monoclonal antibodies and protein S fragments (Dahläck, B., Hildebrand, B. and Malm, J. (1990) *J. Biol. Chem.* 265, 8127–8135).

Binding of mini protein S to C4BP in the presence of calcium (FIG. 3) shows that the mini protein S does not bind to C4BP as the wild type recombinant protein S. This suggests that the SHBG-like domain contains the binding site for C4BP. It further suggests that the SHBG-like domain is probably not involved in the anticoagulant system, but more in the complement system.

Using the ELISA system (FIG. 4), antibody 18 recognized mini protein S equally well as wild type, whereas S7 did not recognize mini protein S. Monoclonal antibody 18 is directed against an epitope in the EGF3 and EGF4 region, whereas monoclonal antibody S7 is directed against an epitope in the SHBG region close to amino acid 460.

Legends to Figures

FIG. 1. SDS/PAGE analysis of immunoblotted protein S. Aliquota (100 ng) of recombinant protein S (lane 1) or mini protein S (lane 2) were separated on a 12.5% SDS gel under reducing conditions and immunoblotted onto immobilon membranes. Bound proteins were detected using rabbit anti-protein S polyclonal antibodies conjugated to peroxidase.

FIG. 2. Protein S cofactor activity to APC: effect of thrombin. The protein S dependent prolongation of the clotting time was measured in an activated partial thromboplastin time system using protein S and C4BP depleted plasma, APC, kaolin and cephalin. Increasing amounts of recombinant protein S (circles), or mini protein S (squares) treated without (open symbols) or with (closed symbols) thrombin were added. Clotting was initiated by the addition of CaCl$_2$ and the clotting time was measured. The experiment was performed in duplicate.

FIG. 3. Binding of mini protein S to C4BP. Anti-C4BP monoclonal antibody 8C11 IgG was coated onto microtitre wells to catch C4BP (1 µg/ml). Recombinant protein S (circles) or mini protein S (squares) were added in increasing amounts in the presence of calcium. Binding to C4BP was for 18 h at room temperature. Bound protein S was detected with anti-protein S 18 IgG conjugated to biotin (0.5 µg/ml). The experiment was performed in duplicate.

Figure 4:
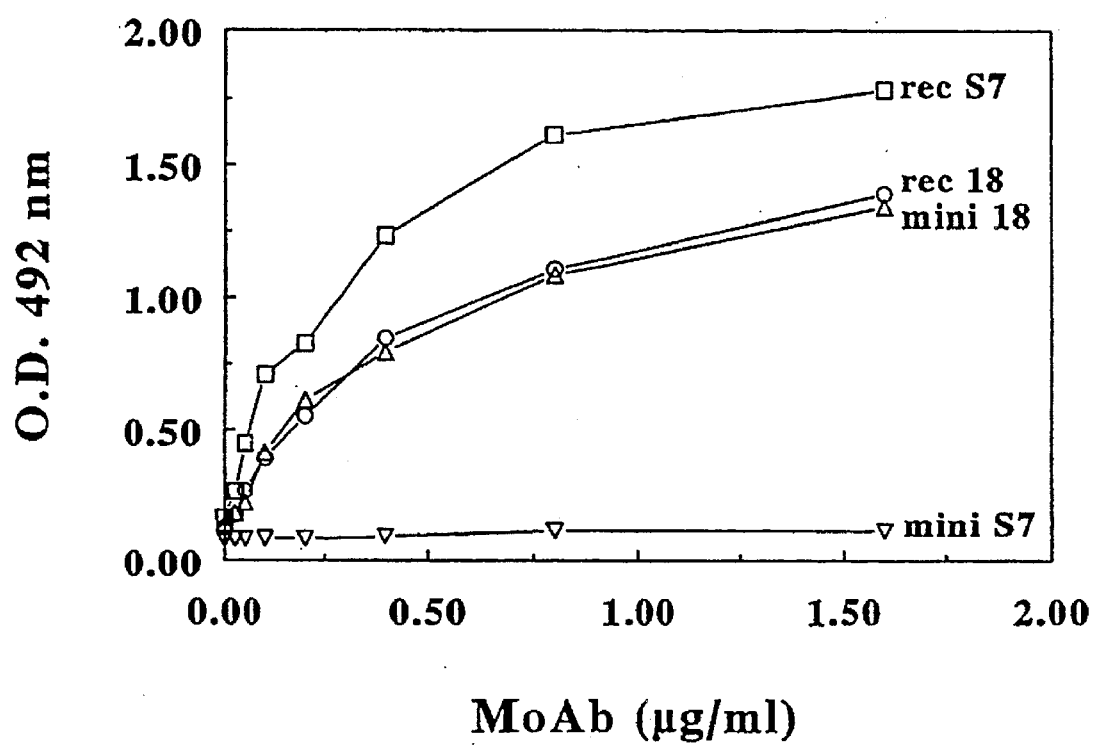

FIG. 4. Binding of mini protein S to different monoclonal antibodies. Microtiter plates were coated with a fixed amount of wild type recombinant (rec) ([], 0) or mini protein S (mini) (Δ, V) and increasing amounts of different monoclonal antibodies S7 ([], V) or 18 (0, Δ) were added for 2 h at room temperature. Bound antibodies were measured using rabbit anti-mouse antibodies conjugated to peroxidase as described in "Experimental Procedures".

Figure 5:
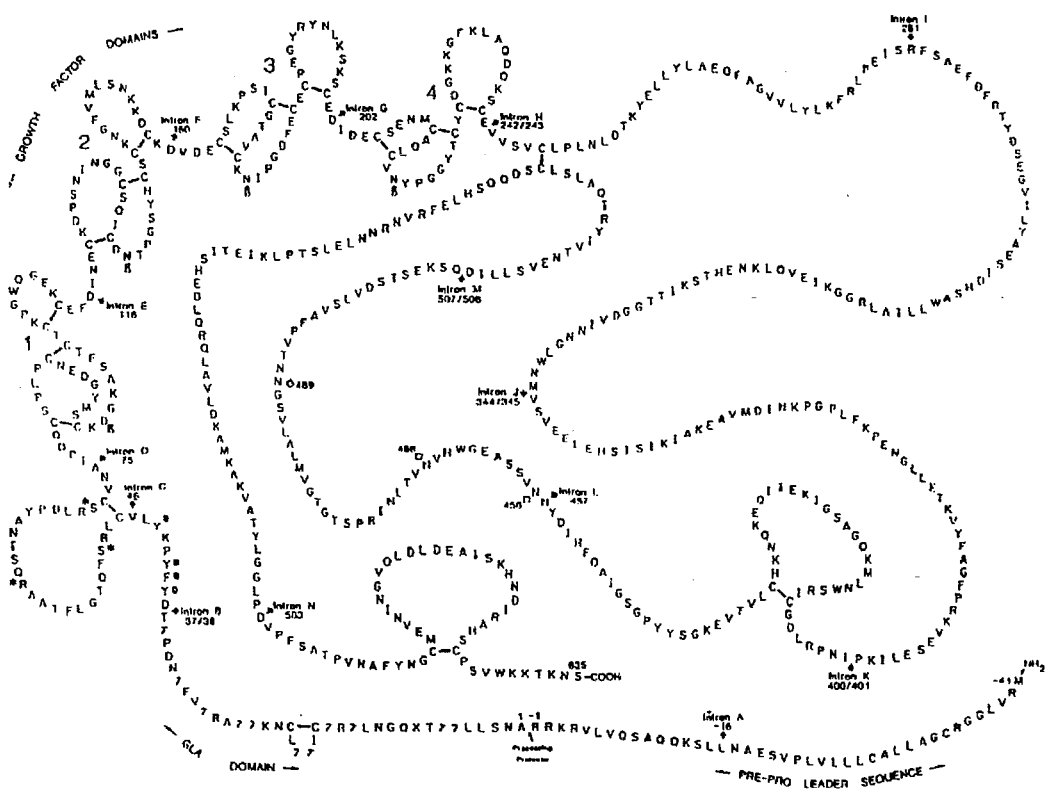

FIG. 5. Primary structure of human protein S. Amino acid sequence (one-letter code) for human prepro protein S and location of the 14 introns (A—N), indicated by solid arrows. The prepro leader sequence includes residues –41 to –1. Solid bars are disulfide bonds; γ, γ, carboxyglutamic acid (GLA); β, β-hydroxyaspartic acid or β-hydroxyasparagine; *, thrombin-cleavage site in the thrombin-sensitive domain; o, aromatic amino acid residues in the aromatic stack domain; open diamonds indicate potential carbohydrate attachment sites of the Asn-X-Ser/Tyr type. Large numbers denote orders of four epidermal growth factor-like domains, which are followed by the sex hormone binding globulin-like domain.

We claim:

1. Deletion mutant of human protein S, having cofactor activity to activated protein C and having at least 95% amino acid residue sequence identity with wild type mature human protein S having the amino acid sequence shown in SEQUENCE ID NO: 2 comprising a deletion of any length in the part of the amino acid sequence located from amino acid residue 243 to the C-terminal amino acid residue, said deletion comprising deletion of at least amino acid residues 408–434 and 600–625.

2. Deletion mutant according to claim 1, lacking at least the amino acid sequence from the C-terminus to residue 401 of the mature wild type human protein S shown in SEQUENCE ID NO: 2.

3. Deletion mutant according to claim 1, lacking the complete sex hormone binding globulin-like domain of the mature wild type protein S shown in SEQUENCE ID NO: 2.

4. Deletion mutant according to claim 1, lacking all amino acid residues from and including 243 to the C terminus of the mature wild type human protein S shown in SEQUENCE ID NO: 2.

5. Deletion mutant according to claim 1, further comprising at least one mutation in the thrombin sensitive loop region selected from positions 49, 60 and 70 of the mature wild type protein S shown in SEQUENCE ID NO: 2, said mutation rendering the deletion mutant thrombin resistant.

6. Deletion mutant according to claim 1, further comprising at least one mutation in epidermal growth factor like domains 3 and 4.

7. A pharmaceutical composition comprising at least a pharmaceutically acceptable carrier and a deletion mutant protein S according to claim 1 as active component.

8. A method for treatment of disease selected from the following: acute thrombosis, protein S deficiency, sepsis, inflammation and cancer comprising administering to a human suffering from said selected disease a therapeutically effective amount of a deletion mutant protein S according to claim 1.

9. Deletion mutant of human protein S according to claim 1 exhibiting at least 95% cofactor activity to activated protein C in comparison to the cofactor activity of human protein S of the wild type shown in SEQUENCE ID NO: 2.

10. Deletion mutant of human protein S, having cofactor activity to activated protein C and having at least 95% amino acid residue sequence identity with wild type mature human protein S having the amino acid sequence shown in SEQUENCE ID NO: 2 comprising a deletion of the amino acid sequence located from amino acid residue 243 to the C-terminal amino acid residue.

* * * * *